United States Patent [19]
Boedecker et al.

[11] Patent Number: 5,378,462
[45] Date of Patent: Jan. 3, 1995

[54] PANCREATIN MICROPELLETS PREPARED WITH POLYETHYLENE GLYCOL 4000, PARAFFIN AND A LOWER ALCOHOL BY EXTRUSION AND ROUNDING

[75] Inventors: Bernd Boedecker, Hannover; Friederike Henninges, Brunswick; Klaus-Juergen Koelln; Guenther Kuhnow, both of Neustadt a. Rbge; Guenter-Josef Peschke, Hanover; Manfred Rehburg, Wagenfeld; Alwin Sobe, Sarstedt; Berthold Stemmle, Burgdorf, all of Germany

[73] Assignee: Kali-Chemie Pharma GmbH, Hanover, Germany

[21] Appl. No.: 109,051

[22] Filed: Aug. 19, 1993

[30] Foreign Application Priority Data

Aug. 19, 1992 [DE] Germany .............................. 4227385

[51] Int. Cl.⁶ ..................... A61K 37/62; A01N 25/34; C12N 11/08; C12N 11/18
[52] U.S. Cl. ................................ 424/94.29; 424/408; 435/175; 435/177; 435/180; 435/182
[58] Field of Search ............... 435/175, 177, 180, 182; 424/94.21, 408

[56] References Cited

U.S. PATENT DOCUMENTS

| | | | |
|---|---|---|---|
| 4,079,125 | 3/1978 | Sipos | 424/32 |
| 4,280,971 | 7/1981 | Wischniewski et al. | 264/15 |
| 5,068,110 | 11/1991 | Fawzi et al. | 424/461 |
| 5,219,572 | 6/1993 | Sivaramakrishnan et al. | 424/438 |
| 5,225,202 | 7/1993 | Hodges et al. | 424/480 |

FOREIGN PATENT DOCUMENTS

| | | |
|---|---|---|
| 21129 | 1/1981 | European Pat. Off. |
| 141607 | 5/1985 | European Pat. Off. |
| 2313916 | 1/1977 | France |

OTHER PUBLICATIONS

Derwent Abstract of JP 4-187,085.

Primary Examiner—David M. Naff
Attorney, Agent, or Firm—Evenson, McKeown, Edwards & Lenahan

[57] ABSTRACT

Pancreatin-containing micropellet cores which can be coated with a gastric juice-resistant film are prepared by extruding a mixture containing pancreatin, polyethylene glycol 4000 and a lower alcohol such as propan-2-ol to produce extrudates which break by themselves into fragments, rounding the fragments with the addition of highly liquid paraffin and drying. Propan-2-ol may be present with the paraffin during rounding. The micropellet cores contain 65–85% pancreatin, and have a bulk density of 0.6 g/ml to 0.85 g/ml, a spherical to ellipsoidal shape with a minor axis in the range of 0.7–1.4 mm and a particle size distribution in which at least 80% of the micropellet cores have a minor axis to major axis ratio in the range from 1:1 to 1:2.

16 Claims, No Drawings

PANCREATIN MICROPELLETS PREPARED WITH POLYETHYLENE GLYCOL 4000, PARAFFIN AND A LOWER ALCOHOL BY EXTRUSION AND ROUNDING

BACKGROUND OF THE INVENTION

The present invention relates to pancreatin-containing micropellets which can be coated with a gastric juice-resistant film and to their production and to pharmaceutical forms containing pancreatin micropellets of this type.

Pancreatin is an enzyme mixture having amylolytic, lipolytic and proteolytic activity. In cases of pancreatic insufficiency, pancreatin can be employed as a pharmaceutically active compound for treating digestive disorders. Since pancreatin is sensitive to gastric juices, it is preferably administered coated with a gastric juice-resistant film, for example in the form of capsules which contain pancreatin pellets coated in a gastric juice-resistant manner. It is desirable that pancreatin-containing particles of this type coated in a gastric juice-resistant manner be as small as possible in order on the one hand to assure a good distribution of the particles in the chyme and an unhindered passage of the particles through the pylorus and on the other hand to achieve a bulk density of the pancreatin pellets which is as high as possible in order to be able to accommodate as many pancreatin pellets as possible in the capsules per unit of capsule volume.

German Patent No. DE 2,923,279 describes a process for producing pancreatin pellets in which a moldable mass of pancreatin and organic solvents is extruded in an extruding press, and the extrudate is cut up into angular extrudate cuttings which can be rounded off by pelletization with the addition of pancreatin powder.

There remained a need, however, for improved pancreatin micropellets having a high bulk density and a small particle size.

SUMMARY OF THE INVENTION

It is therefore the object of the invention to provide pancreatin micropellets which have a high bulk density and a small particle size.

Another object of the invention is to provide pancreatin micropellets which can be coated with a gastric juice-resistant coating.

It is also an object of the invention to provide an improved process for producing pancreatin micropellets.

These and other objects of the invention are achieved by providing a pancreatin micropellet core which can be coated with a gastric juice-resistant film, the micropellet core having a pancreatin content of 65-85 wt-% and a bulk density of 0.6 g/ml to 0.85 g/ml; consisting essentially of 100 parts by weight pancreatin, from 15 to 50 parts by weight polyethylene glycol 4000 and from 1.5 to 5 parts by weight of highly liquid paraffin, and having a spherical to ellipsoidal shape with a minimum diameter in the range from 0.7-1.4 mm, and a particle size distribution in which at least 80% of the particles have a minor axis to major axis ratio in the range from 1:1 to 1:2.

In accordance with a further aspect of the invention, the objects are also achieved by providing a process for producing pancreatin micropellet cores which can be coated with a gastric juice-resistant film and having a pancreatin content of 65-85 wt-%, comprising the steps of:

a) mixing 100 parts by weight of pancreatin with from 15 to 50 parts by weight of polyethylene glycol 4000 and a sufficient amount of a lower alcohol to achieve an extrudable consistency, to form an extrudable mixture, b) pressing the extrudable mixture in an extruding press containing a piercing die having a hole diameter of 0.8-1.2 mm to form extrudates, and collecting extrudate fragments of a length suitable for transfer to a rounding apparatus, and c) transferring the collected extrudate fragments to a rounding apparatus and breaking up the transferred fragments in said rounding apparatus with the addition of from 1.5 to 5 parts by weight of liquid paraffin and from 1.5 to 10 parts by weight of propan-2-ol, per 100 parts by weight of pancreatin, under conditions which round off fracture edges, to form micropellet cores having a spherical to ellipsoidal shape and a particle size distribution in which at least 80% of the particles have a minor axis to major axis ratio in the range from 1:1 to 1:2, and d) drying the micropellet cores obtained in step c) at a temperature in the range from 30° to 50° C.

DETAILED DESCRIPTION OF PREFERRED EMBODIMENTS

An improved process has now been found with which novel gastric juice-resistant film-coated pancreatin micropellets can be produced having a high bulk density and a small particle size assuring good passage through the pylorus.

The present invention therefore relates to novel pancreatin micropellet cores which can be coated with a gastric juice-resistant film and having a pancreatin content of 65-85, in particular 75-80, % by weight, characterized in that they have a bulk density of 0.6 g/ml to 0.85 g/ml and in that they consist essentially of pancreatin, polyethylene glycol 4000 and highly liquid paraffin and contain, relative to 100 parts by weight of pancreatin, 15-50, in particular 20-30, parts by weight of polyethylene glycol 4000 and 1.5-5, in particular 2-3, parts by weight of highly liquid paraffin and in that they have a spherical to ellipsoidal shape, the sphere diameter or the minor axis being in the range 0.7-1.4 mm, in particular 0.8-1.2 mm, and have a particle size distribution in which at least 80% of the pancreatin micropellet cores have a ratio of the minor axis to the major axis in the range from 1:1 to 1:2.

The invention further relates to gastric juice-resistant film-coated pancreatin pellets which consist of the aforementioned pancreatin micropellet cores and a gastric juice-resistant film coating.

The invention furthermore relates to a process for the production of the pancreatin micropellet cores described above which can be coated with a gastric juice-resistant film, characterized in that a) 100 parts by weight of pancreatin and mixed with 15-50, in particular 20-30, parts by weight of polyethylene glycol 4000 and an amount of a lower alcohol, in particular propan-2-ol, sufficient for achieving an extrudable consistency, to give an extrudable mixture, b) the extrudable mixture is pressed in an extruding press containing a piercing die having a hole diameter suitable for achieving the aforementioned pellet-core diameter range, in particular a hole diameter of 0.8–1.2 mm, to give extrudates, and extrudate fragments of a length suitable for transfer to a rounding apparatus are taken from the press and c) the extrudate fragments are transferred to a rounding apparatus and broken up therein with addition of 1.5–5, in particular 2–3, parts by weight of highly liquid paraffin and 1.5–10, in particular 2–6, parts by weight of propan-2-ol, in each case relative to 100 parts by weight of pancreatin, under conditions which round fracture edges, to give micropellet cores of spherical to ellipsoidal shape having a particle size distribution in which at least 80% of the particles have a ratio of the minor axis to the major axis in the range 1:1 to 1:2, and d) the micropellet cores obtained in c) are dried at temperatures in the range 30°–50° C.

Pancreatin micropellet cores are obtained by the process according to the invention which can subsequently be coated with a gastric juice-resistant film in a known manner to produce gastric juice-resistant film-coated pancreatin micropellets. In the process according to the invention, the pancreatin is first mixed with the polyethylene glycol and a lower alcohol, preferably propan-2-ol, to give an extrudable mixture. Preferably, 25 (±20%) parts by weight of polyethylene glycol 4000 are employed relative to 100 parts by weight of pancreatin. The propan-2-ol used as granulating liquid, which is then evaporated again and/or removed by drying, is added in an amount such that the mixture is sufficiently moistened in order to yield an extrudable mass. In general, this is achieved using 10–30 parts by weight, preferably 15–25 parts by weight, of propan-2-ol relative to 100 parts by weight of pancreatin.

If desired, other known pharmaceutically customary adjuvants such as, e.g., customary preservatives such as parahydroxybenzoic acid esters, can also be added to the extrudable mixture.

The extrudable mixture is then extruded in a known manner in a known extruding press, which is fitted with a piercing die having a hole diameter in the range from 0.8 to 1.2 mm. In order to avoid damage to the enzymes which could result from the heat of compression which arises during the extrusion, the heat of compression can be dissipated by additional cooling devices on the extruding press, and the mixture to be extruded can be pre-cooled, if desired. The machine throughput depends on the size of the extruder and on the pancreatin quality. Typical machine throughputs may range, for example, from 15 to 150 kg per hour.

The cross-sectional strength of the extrudates emerging from the piercing die is small enough that the extrudates can be broken up by themselves while still in the extruding press into extrudate segments having a length suitable for transfer to a rounding apparatus. On the other hand, the cross-sectional strength of the extrudates is high enough that excessive crumbling and formation of an undesirably high fines content does not occur. If desired, the fragment length can be controlled by mounting a breaking or cutting device for the extrudates in the extruding press after the piercing die.

The cross-sectional strength of the extrudate fragments is such that on further treatment in a rounding apparatus, for example a commercially available spheronizer, they break up further to give particles of the desired pellet size. In this case, the length of the extrudate fragments is not critical for further processing in the rounding apparatus. However, in order to assure an unhindered supply of the extrudate fragments to the rounding apparatus, it is desirable that the length of at least the main portion of the extrudate fragments does not exceed 5 cm, and is preferably in the range between 0.5 and 3 cm, in order to avoid a greater locking together of the extrudate fragments with one another and thus a disturbance in the uniform transfer of the material to the rounding apparatus.

The extrudate fragments are treated in the rounding apparatus in a known manner. In this process, the extrudate fragments are further broken up into small particles and these are rounded. For each 100 parts by weight of pancreatin, from 1.5 to 5, in particular from 2 to 3, parts by weight of highly liquid paraffin and an amount of propan-2-ol, sufficient to compensate for evaporation during the residence time in the rounding apparatus are simultaneously added to the extrudate fragments in the rounding apparatus. The amount of propan-2-ol added per 100 parts by weight of pancreatin may be in the range from 1.5 to 10, in particular from 2 to 6, parts by weight.

Surprisingly, the cross-sectional strength of the extrudate fragments is such that, on further breaking up in the rounding apparatus, particles with a spherical to ellipsoidal shape having a very narrow particle size spectrum result, in which at least 80% of the particles formed have a minor axis to major axis ratio of 1:1 to 1:2. The rounding-off of the particles is also satisfactory.

After rounding-off, the still moist round pellets are dried at 30°–50° C., in particular at 40° C., in a conventional drying unit, for example a shelf dryer, in order to substantially remove propan-2-ol from the round pellets. Drying is customarily carried out until the propan-2-ol content in the round pellets is less than or equal to 1%. Pancreatin micropellet cores which can be coated with a gastric juice-resistant film can thus be obtained in a problem-free manner by means of the process according to the invention.

The combination, according to the invention, of the composition of the mixture to be extruded and the small cross-section of the extrudates leads to the result that the extrudate obtained when extruding in the extruding press is produced in the form of extrudates whose cross-sectional strength is precisely adjusted so that the extrudates have an adequate susceptibility to division in order to be able to break up in the extruding press into extrudate fragments having a length suitable for transfer to a rounding apparatus and when the extrudate fragments are treated in the rounding apparatus, they break up further to give particles which exhibit the aforementioned narrow particle size spectrum and which have a consistency such that they can be adequately rounded during treatment in the rounding apparatus so that no sharp edges or cavities remain on the resulting pellets, and they can then be coated with a film without any difficulty. It is surprising that according to the invention an extrudate is produced which has exactly the right degree of brittleness so that further processing results in micropellet cores of the desired size, which have good rounding properties. It is also highly surprising that micropellet cores can be produced without any damage to the enzyme activity of the pancreatin occurring in the case of extruding press agglomeration as a result of piercing dies having so small a diameter, in which high compression pressures occur, and without the extrudate being hardened in such a way that when the extrudate is subsequently treated in the rounding apparatus, the further break up of the fragments into the desired micropellet core sizes and the rounding-off of the fracture edges being prevented by the material becoming too hard so that satisfactory shaping would no longer take place.

The process according to the invention thus offers the advantage that during extrusion pressing, extrudate agglomerates are obtained which can break up without an additional cutting operation to give extrudate fragments of suitable length for further processing and these can be further broken into particles of the desired micropellet size having a surprisingly narrow particle size spectrum and good rounding-off properties during subsequent treatment without a further process step. At the same time, a high yield of micropellet cores is achieved by avoiding production of a fines content and by the achievement of a narrow particle size spectrum. Despite the small hole diameters of the piercing die, a high pelletizing efficiency can be achieved.

The pancreatin micropellet cores obtained according the invention can be provided with a gastric juice-resistant coating in a known manner. For example, the pancreatin micropellet cores can be coated with known gastric juice-resistant film-forming agents such as, e.g., hydroxypropylmethylcellulose acetate succinate (=HPMCAS), hydroxypropylmethylcellulose phthalate (=HPMCP), cellulose acetate phthalate (=CAP) or polyvinyl acetate phthalate (=PVAP). Copolymers known as customary film-forming agents such as, for example, methacrylic acid/methyl methacrylate copolymers or methacrylic acid/ethyl acrylate copolymers, and also be used. The film-forming agents can be applied to the pancreatin micropellet cores according to the invention using known types of film-coating apparatus, e.g. coaters, in the customary use forms, e.g. as organic solutions or organic or aqueous dispersions, optionally with addition of a conventional plasticizer.

The resulting gastric juice-resistant film-coated pancreatin micropellets are distinguished by a high bulk density, for example in the range from 0.6 g/ml to 0.85 g/ml, which makes it possible to increase the filling weight per capsule and thus the active compound content of each capsule.

The following example is intended to illustrate the invention in greater detail without limiting its scope.

EXAMPLE 120 kg of pancreatin were mixed with 30 kg of polyethylene glycol 4000 in a commercially available mixer and thoroughly moistened with about 20 kg of propan-2-ol.

The mixture was pressed by means of an extruding press (extruder) which was equipped with a piercing die having 0.8 mm internal diameter bores and a cutting device arranged downstream. In this process extrudate fragments having an extrudate length of up to 20 mm were obtained.

Portions of about 15 kg each of the extrudate fragments were broken up in a rounding apparatus (Caleva type) and rounded off to give spherically shaped pellets, a further 300 g of highly liquid paraffin and, depending on the residence time in the rounding apparatus (3-6 min.), approximately a further 300 to 700 g of propan-2-ol being added to each portion.

After drying in a commercially available shelf dryer, about 90% of pancreatin micropellet cores having a diameter of 0.7 to 1.4 mm, graded with a 0.7 mm sieve (sieving of undersize grain <0.7 mm) and a 1.4 mm sieve (sieving of oversize grain >1.4 mm), having a pancreatin content of about 78% were obtained as the product. The bulk density was 0.7 g/ml.

The micropellet cores were then coated in a known manner in a conventional film-coating apparatus with a solution of hydroxypropylmethylcellulose phthalate (type HP55), dibutyl phthalate, highly liquid paraffin and silicone oil (Dimethicone 1000) in acetone. About 90% of gastric juice-resistant pancreatin micropellets, having a diameter in the range from 0.7 to 1.6 mm, graded with a 0.7 mm sieve (sieving of undersize grain <0.7 mm) and a 1.6 mm sieve (sieving of oversize grain >1.6 mm) having a content of about 60% pancreatin, relative to the film-coated micropellets, and a bulk density of 0.8 g/ml were obtained as the product.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A pancreatin micropellet core which can be coated with a gastric juice-resistant film, said micropellet core having a pancreatin content of 65-85 wt-% and a bulk density of 0.6 g/ml to 0.85 g/ml; obtained by extruding a mixture consisting essentially of 100 parts by weight pancreatin, from 15 to 50 parts by weight polyethylene glycol 4000 and sufficient lower alcohol to achieve an extrudable consistency through a die having a hole diameter of 0.8 to 1.2 mm to yield extrudates which break by themselves into extrudate fragments of a length suitable for transfer to a rounding apparatus; thereafter rounding the extrudate fragments with the addition of from 1.5 to 5 parts by weight of highly liquid paraffin, the resulting rounded fragments having a spherical to ellipsoidal shape with a minimum diameter in the range from 0.7-1.4 mm, and a particle size distribution in which at least 80% of the pancreatin micropellet cores have a minor axis to major axis ratio in the range from 1:1 to 1:2, and drying the rounded fragments to remove the alcohol.

2. The pancreatin micropellet core according to claim 1, having a pancreatin content of from 75 to 80 wt-%.

3. The pancreatin micropellet core according to claim 1, containing from 20 to 30 parts by weight polyethylene glycol 4000 and from 2 to 3 parts by weight highly liquid paraffin per 100 parts of pancreatin.

4. The pancreatin micropellet core according to claim 1, having a minimum diameter in the range from 0.8 to 1.2 mm.

5. The pancreatin micropellet core according to claim 1 coated with a gastric juice-resistant film.

6. A process for producing pancreatin micropellet cores which can be coated with a gastric juice-resistant film and having a pancreatin content of 65-85 wt-%, said process comprising the steps of:
   a) mixing 100 parts by weight of pancreatin with from 15 to 50 parts by weight of polyethylene glycol 4000 and a sufficient amount of a lower alcohol to achieve an extrudable consistency, to form an extrudable mixture,
   b) pressing said extrudable mixture in an extruding press containing a piercing die having a hole diameter of 0.8-1.2 mm to form extrudates which break by themselves into extrudate fragments of a length suitable for transfer to a rounding apparatus, and c) transferring the extrudate fragments to a rounding apparatus and breaking up the transferred fragments in said rounding apparatus with the addition of from 1.5 to 5 parts by weight of liquid paraffin and from 1.5 to 10 parts by weight of propan-2-ol, per 100 parts by weight of pancreatin, under conditions which round fracture edges, to form micropellet cores having a spherical to ellipsoidal shape and a particle size distribution in which at least 80% of the particles have a minor axis to major axis ratio in the range from 1:1 to 1:2, and d) drying the micropellet cores obtained in step c) at a temperature in the range from 30° to 50° C.

7. The process according to claim 6, wherein said micropellet cores have a pancreatin content of from 75 to 80 wt-%.

8. The process according to claim 6, wherein 100 parts by weight pancreatin are mixed with from 20 to 30 parts by weight polyethylene glycol 4000.

9. The process according to claim 6, wherein in step c) 2-3 parts by weight of liquid paraffin and 2-6 parts by weight of propan-2-ol are added per 100 parts by weight pancreatin.

10. The process according to claim 6, wherein the extrudate fragments collected from the extruding press have a length of at most 5 cm.

11. The process according to claim 10, wherein the extrudate fragments collected from the extruding press have a length in the range from 0.5 to 3 cm.

12. The process according to claim 6, wherein in step b), the extrudate fragments are divided by a cutting apparatus located after the piercing die before the fragments are transferred to the rounding apparatus.

13. The process according to claim 6, wherein said lower alcohol is propan-2-ol.

14. The process according to claim 13, wherein in step a) from 10 to 30 parts by weight propan-2-ol are admixed per 100 parts by weight pancreatin.

15. The process according to claim 14, wherein in step a) from 15 to 25 parts by weight propan-2-ol are admixed per 100 parts by weight pancreatin.

16. The process according to claim 6, further comprising coating the pancreatin micropellet cores obtained in step c) with a gastric juice-resistant film prior to said drying step.

* * * * *